(12) United States Patent
Tupin, Jr. et al.

(10) Patent No.: US 11,317,608 B2
(45) Date of Patent: *May 3, 2022

(54) ANIMAL HEALTH AND WELLNESS MONITORING USING UWB RADAR

(71) Applicant: i4C Innovations Inc., Chantilly, VA (US)

(72) Inventors: Joe Paul Tupin, Jr., Round Hill, VA (US); John Michael Couse, Toronto (CA)

(73) Assignee: i4C Innovations Inc., Cazenovia, NY (US)

( * ) Notice: Subject to any disclaimer, the term of this patent is extended or adjusted under 35 U.S.C. 154(b) by 637 days.

This patent is subject to a terminal disclaimer.

(21) Appl. No.: 15/998,526

(22) Filed: Aug. 16, 2018

(65) Prior Publication Data

US 2019/0191670 A1     Jun. 27, 2019

Related U.S. Application Data

(63) Continuation of application No. 15/377,281, filed on Dec. 13, 2016, now Pat. No. 10,070,627, which is a
(Continued)

(51) Int. Cl.
*A01K 29/00*      (2006.01)
*A61B 5/0507*      (2021.01)
(Continued)

(52) U.S. Cl.
CPC .......... *A01K 29/005* (2013.01); *A01K 27/009* (2013.01); *A61B 5/0205* (2013.01);
(Continued)

(58) Field of Classification Search
CPC .... A01K 29/00; A01K 27/001; A01K 29/005; A01K 27/002; A01K 27/009; A61B 2503/40; A61B 5/0205; A61B 5/02438; A61B 5/0507; A61B 5/0816; A61B 5/1107; A61B 5/6822; A61B 5/6824;
(Continued)

(56) References Cited

U.S. PATENT DOCUMENTS

| 4,527,240 A | 7/1985 | Kvitash |
| 4,930,519 A | 6/1990 | Anderson et al. |

(Continued)

FOREIGN PATENT DOCUMENTS

| CA | 1296068 C | 2/1992 |
| CA | 2 485 129 A1 | 5/2005 |

(Continued)

OTHER PUBLICATIONS

Sep. 28, 2018—(NZ) Examination Report—App 734823.
(Continued)

*Primary Examiner* — Trinh T Nguyen
(74) *Attorney, Agent, or Firm* — Banner & Witcoff, Ltd.

(57) ABSTRACT

A collar with an ultra-wideband radar is described. A housing contains sensor electronics and the transmit and receive antennas are located separate from the housing around the circumference of the collar. A first example of the collar includes a first transmit antenna and a first receive antenna. A second example of the collar adds a second transmit antenna and a second receive antenna.

14 Claims, 12 Drawing Sheets

Related U.S. Application Data continuation of application No. 14/086,721, filed on Nov. 21, 2013, now Pat. No. 9,526,437.

(60) Provisional application No. 61/729,298, filed on Nov. 21, 2012.

(51) Int. Cl.

| | | |
|---|---|---|
| *A61B 5/0205* | (2006.01) | |
| *A61B 5/024* | (2006.01) | |
| *A61B 5/08* | (2006.01) | |
| *A61B 5/11* | (2006.01) | |
| *A01K 27/00* | (2006.01) | |
| *A61B 5/00* | (2006.01) | |
| *G01S 13/88* | (2006.01) | |
| *G01S 13/02* | (2006.01) | |

(52) U.S. Cl.
CPC ........ *A61B 5/02438* (2013.01); *A61B 5/0507* (2013.01); *A61B 5/0816* (2013.01); *A61B 5/1107* (2013.01); *A61B 5/6822* (2013.01); *A61B 5/6831* (2013.01); *G01S 13/0209* (2013.01); *G01S 13/88* (2013.01); *A61B 2503/40* (2013.01)

(58) Field of Classification Search
CPC . A61B 5/6825; A61B 5/6831; G01S 13/0209; G01S 13/88
See application file for complete search history.

(56) References Cited

U.S. PATENT DOCUMENTS

| | | |
|---|---|---|
| 5,037,305 A | 8/1991 | Aleck |
| 5,289,163 A | 2/1994 | Perez et al. |
| 5,389,934 A | 2/1995 | Kass |
| 5,461,365 A | 10/1995 | Schlager et al. |
| 5,650,770 A | 7/1997 | Schlager et al. |
| 5,772,585 A | 6/1998 | Lavin et al. |
| 6,193,654 B1 | 2/2001 | Richardson et al. |
| 6,198,390 B1 | 3/2001 | Schlager et al. |
| 6,238,354 B1 | 5/2001 | Alvarez |
| 6,366,871 B1 | 4/2002 | Geva |
| 6,402,692 B1 | 6/2002 | Morford |
| 6,497,656 B1 | 12/2002 | Evans et al. |
| 6,518,889 B2 | 2/2003 | Schlager et al. |
| 6,616,607 B2 | 9/2003 | Hashimoto et al. |
| 6,693,585 B1 | 2/2004 | MacLeod |
| 6,697,103 B1 | 2/2004 | Fernandez et al. |
| 6,723,055 B2 | 4/2004 | Hoffman |
| 6,730,023 B1 | 5/2004 | Dodds |
| 6,733,464 B2 | 5/2004 | Olbrich et al. |
| 6,811,113 B1 | 11/2004 | Silansky et al. |
| 6,847,892 B2 | 1/2005 | Zhou et al. |
| 6,889,135 B2 | 5/2005 | Curatolo et al. |
| 6,893,396 B2 | 5/2005 | Schulze et al. |
| 6,910,050 B2 | 6/2005 | Pawlick |
| 6,941,239 B2 | 9/2005 | Unuma et al. |
| 6,988,026 B2 | 1/2006 | Breed et al. |
| 7,020,508 B2 | 3/2006 | Stivoric et al. |
| 7,089,099 B2 | 8/2006 | Shostak et al. |
| 7,154,398 B2 | 12/2006 | Chen et al. |
| 7,187,960 B2 | 3/2007 | Abreu |
| 7,196,628 B2 | 3/2007 | Hixson |
| 7,218,242 B2 | 5/2007 | Scalisi et al. |
| 7,261,690 B2 | 8/2007 | Teller et al. |
| 7,265,666 B2 | 9/2007 | Daniel |
| 7,282,028 B2 | 10/2007 | Kim et al. |
| 7,285,090 B2 | 10/2007 | Stivoric et al. |
| 7,297,110 B2 | 11/2007 | Goyal et al. |
| 7,299,159 B2 | 11/2007 | Nanikashvili |
| 7,330,784 B2 | 2/2008 | Johnson et al. |
| 7,335,168 B2 | 2/2008 | Rugg |
| 7,371,214 B2 | 5/2008 | Kouchi et al. |
| 7,380,518 B2 | 6/2008 | Kates |
| 7,396,331 B2 | 7/2008 | Mack et al. |
| 7,399,220 B2 | 7/2008 | Kriesel et al. |
| 7,399,277 B2 | 7/2008 | Saidara et al. |
| 7,423,526 B2 | 9/2008 | Despotis |
| 7,427,920 B2 | 9/2008 | Martin et al. |
| 7,467,034 B2 | 12/2008 | Breed et al. |
| 7,467,809 B2 | 12/2008 | Breed et al. |
| 7,482,935 B2 | 1/2009 | Lee |
| 7,492,251 B1 | 2/2009 | Katz |
| 7,527,288 B2 | 5/2009 | Breed |
| 7,539,532 B2 | 5/2009 | Tran |
| 7,539,533 B2 | 5/2009 | Tran |
| 7,558,622 B2 | 7/2009 | Tran |
| 7,589,638 B2 | 9/2009 | Jackson et al. |
| 7,610,094 B2 | 10/2009 | Stahmann et al. |
| 7,616,110 B2 | 11/2009 | Crump et al. |
| 7,650,210 B2 | 1/2010 | Breed |
| 7,659,826 B2 | 2/2010 | Humbard |
| 7,675,410 B2 | 3/2010 | Aritsuka et al. |
| 7,679,504 B2 | 3/2010 | Wang et al. |
| 7,689,437 B1 | 3/2010 | Teller et al. |
| 7,691,068 B2 | 4/2010 | Felder et al. |
| 7,705,736 B1 | 4/2010 | Kedziora |
| 7,712,365 B1 | 5/2010 | James |
| 7,728,724 B1 | 6/2010 | Scalisi et al. |
| 7,734,061 B2 | 6/2010 | Breed et al. |
| 7,761,312 B2 | 7/2010 | Brown |
| 7,785,257 B2 | 8/2010 | Mack et al. |
| 7,800,506 B2 | 9/2010 | Zehavi |
| 7,826,983 B2 | 11/2010 | Alwan et al. |
| 7,830,962 B1 | 11/2010 | Fernandez et al. |
| 7,843,350 B2 | 11/2010 | Geissler et al. |
| 7,857,771 B2 | 12/2010 | Alwan et al. |
| 7,860,731 B2 | 12/2010 | Jackson et al. |
| 7,867,141 B2 | 1/2011 | Matsumura et al. |
| 7,889,069 B2 | 2/2011 | Fifolt et al. |
| 7,905,832 B1 | 3/2011 | Lau et al. |
| 7,949,405 B2 | 5/2011 | Feher |
| 7,999,741 B2 | 8/2011 | Graves et al. |
| 8,015,026 B2 | 9/2011 | Schweisguth et al. |
| 8,019,501 B2 | 9/2011 | Breed |
| 8,019,633 B2 | 9/2011 | Stroman et al. |
| 8,033,996 B2 | 10/2011 | Behar |
| 8,036,851 B2 | 10/2011 | Vock et al. |
| 8,060,109 B2 | 11/2011 | Fomukong et al. |
| 8,073,707 B2 | 12/2011 | Teller et al. |
| 8,094,009 B2 | 1/2012 | Allen et al. |
| 8,102,256 B2 | 1/2012 | Scalisi et al. |
| 8,103,333 B2 | 1/2012 | Tran |
| 8,121,673 B2 | 2/2012 | Tran |
| 8,125,331 B2 | 2/2012 | Allen et al. |
| 8,125,332 B2 | 2/2012 | Curran et al. |
| 8,157,730 B2 | 4/2012 | LeBoeuf et al. |
| 8,170,609 B2 | 5/2012 | Hedtke et al. |
| 8,172,777 B2 | 5/2012 | Goto |
| 8,195,188 B2 | 6/2012 | Fomukong et al. |
| 8,204,786 B2 | 6/2012 | LeBoeuf et al. |
| 8,214,007 B2 | 7/2012 | Baker et al. |
| 8,224,355 B2 | 7/2012 | Beydler et al. |
| 8,248,231 B2 | 8/2012 | Taylor |
| 8,255,238 B2 | 8/2012 | Powell et al. |
| 8,271,015 B2 | 9/2012 | Aoki et al. |
| 8,284,046 B2 | 10/2012 | Allen et al. |
| 8,297,231 B2 | 10/2012 | Yanai et al. |
| 8,305,220 B2 | 11/2012 | Gibson |
| 8,308,641 B2 | 11/2012 | Moroney, III et al. |
| 8,323,188 B2 | 12/2012 | Tran |
| 8,328,718 B2 | 12/2012 | Tran |
| 2001/0044588 A1 | 11/2001 | Mault |
| 2001/0049471 A1 | 12/2001 | Suzuki et al. |
| 2002/0010390 A1 | 1/2002 | Guice et al. |
| 2002/0019584 A1 | 2/2002 | Schulze et al. |
| 2002/0021219 A1 | 2/2002 | Edwards |
| 2002/0115915 A1 | 8/2002 | Pratt et al. |
| 2002/0143241 A1 | 10/2002 | Thorell |
| 2002/0154015 A1 | 10/2002 | Hixson |
| 2003/0004403 A1 | 1/2003 | Drinan et al. |
| 2003/0139655 A1 | 7/2003 | Dodds |

(56) References Cited

U.S. PATENT DOCUMENTS

| | | |
|---|---|---|
| 2003/0166996 A1 | 9/2003 | Kim et al. |
| 2003/0210147 A1 | 11/2003 | Humbard |
| 2004/0027246 A1 | 2/2004 | Aguglia |
| 2004/0061606 A1 | 4/2004 | Gronvold |
| 2004/0087878 A1 | 5/2004 | Krausman et al. |
| 2004/0100376 A1 | 5/2004 | Lye et al. |
| 2004/0130446 A1 | 7/2004 | Chen et al. |
| 2004/0148140 A1 | 7/2004 | Tarassenko et al. |
| 2005/0090718 A1 | 4/2005 | Dodds |
| 2005/0099294 A1 | 5/2005 | Bogner et al. |
| 2005/0101843 A1 | 5/2005 | Quinn et al. |
| 2005/0124864 A1 | 6/2005 | Mack et al. |
| 2005/0134452 A1 | 6/2005 | Smith |
| 2005/0197546 A1 | 9/2005 | Mardiks et al. |
| 2005/0234310 A1 | 10/2005 | Alwan et al. |
| 2006/0006999 A1 | 1/2006 | Walczyk et al. |
| 2006/0106289 A1 | 5/2006 | Elser et al. |
| 2006/0111642 A1 | 5/2006 | Baura et al. |
| 2006/0155172 A1 | 7/2006 | Rugg |
| 2006/0173363 A1 | 8/2006 | Felder et al. |
| 2006/0195050 A1 | 8/2006 | Alwan et al. |
| 2006/0253005 A1 | 11/2006 | Drinan et al. |
| 2006/0255935 A1 | 11/2006 | Scalisi et al. |
| 2006/0258914 A1 | 11/2006 | Derchak et al. |
| 2006/0264730 A1 | 11/2006 | Stivoric et al. |
| 2007/0004969 A1 | 1/2007 | Kong et al. |
| 2007/0027365 A1 | 2/2007 | Kosted |
| 2007/0060800 A1 | 3/2007 | Drinan et al. |
| 2007/0185390 A1 | 8/2007 | Perkins et al. |
| 2007/0229350 A1 | 10/2007 | Scalisi et al. |
| 2007/0232351 A1 | 10/2007 | Scalisi et al. |
| 2007/0233403 A1 | 10/2007 | Alwan et al. |
| 2007/0255115 A1 | 11/2007 | Anglin et al. |
| 2007/0255122 A1 | 11/2007 | Vol et al. |
| 2007/0270668 A1 | 11/2007 | Childre et al. |
| 2007/0276270 A1 | 11/2007 | Tran |
| 2007/0282177 A1 | 12/2007 | Pilz |
| 2007/0293781 A1 | 12/2007 | Sims et al. |
| 2008/0058670 A1 | 3/2008 | Mainini |
| 2008/0129518 A1 | 6/2008 | Carlton-Foss |
| 2008/0154098 A1 | 6/2008 | Morris et al. |
| 2008/0255438 A1 | 10/2008 | Saidara et al. |
| 2008/0269625 A1 | 10/2008 | Halperin et al. |
| 2008/0281164 A1 | 11/2008 | Stebor et al. |
| 2008/0281633 A1 | 11/2008 | Burdea et al. |
| 2008/0287751 A1 | 11/2008 | Stivoric et al. |
| 2008/0312511 A1 | 12/2008 | Osler et al. |
| 2009/0066519 A1 | 3/2009 | Martino |
| 2009/0099967 A1 | 4/2009 | Yokota et al. |
| 2009/0103722 A1 | 4/2009 | Anderson et al. |
| 2009/0105605 A1 | 4/2009 | Abreu |
| 2009/0112071 A1 | 4/2009 | LeBoeuf et al. |
| 2009/0119119 A1 | 5/2009 | Scalisi et al. |
| 2009/0131759 A1 | 5/2009 | Sims et al. |
| 2009/0137881 A1 | 5/2009 | Ebert et al. |
| 2009/0146822 A1 | 6/2009 | Soliman |
| 2009/0174603 A1 | 7/2009 | Scalisi et al. |
| 2009/0189807 A1 | 7/2009 | Scalisi et al. |
| 2009/0216556 A1 | 8/2009 | Martin et al. |
| 2009/0234198 A1 | 9/2009 | Vorse |
| 2009/0267829 A1 | 10/2009 | Mitchell et al. |
| 2009/0287120 A1 | 11/2009 | Ferren et al. |
| 2009/0289844 A1 | 11/2009 | Palsgrave et al. |
| 2009/0292214 A1 | 11/2009 | Ferren et al. |
| 2009/0292219 A1 | 11/2009 | Pringle et al. |
| 2009/0292222 A1 | 11/2009 | Ferren et al. |
| 2009/0312660 A1 | 12/2009 | Guarino et al. |
| 2009/0315767 A1 | 12/2009 | Scalisi et al. |
| 2009/0318778 A1 | 12/2009 | Dacso et al. |
| 2010/0016745 A1 | 1/2010 | Crump et al. |
| 2010/0030036 A1 | 2/2010 | Mottram et al. |
| 2010/0036277 A1 | 2/2010 | Austin |
| 2010/0055734 A1 | 3/2010 | Everson |
| 2010/0060642 A1 | 3/2010 | Chhaparwal et al. |
| 2010/0109875 A1 | 5/2010 | Ayon et al. |
| 2010/0121156 A1 | 5/2010 | Yoo |
| 2010/0168589 A1 | 7/2010 | Banet et al. |
| 2010/0179438 A1 | 7/2010 | Heneghan et al. |
| 2010/0198024 A1 | 8/2010 | Elazari-Volcani et al. |
| 2010/0214090 A1 | 8/2010 | Sartini et al. |
| 2010/0222686 A1 | 9/2010 | Fisher et al. |
| 2010/0231391 A1 | 9/2010 | Dror et al. |
| 2010/0261981 A1 | 10/2010 | Griffioen |
| 2010/0302042 A1 | 12/2010 | Barnett et al. |
| 2010/0312071 A1 | 12/2010 | Schenk |
| 2010/0321189 A1 | 12/2010 | Gibson |
| 2011/0004072 A1 | 1/2011 | Fletcher et al. |
| 2011/0015504 A1 | 1/2011 | Yoo |
| 2011/0025493 A1 | 2/2011 | Papadopoulos et al. |
| 2011/0028798 A1 | 2/2011 | Hyde et al. |
| 2011/0028799 A1 | 2/2011 | Hyde et al. |
| 2011/0029038 A1 | 2/2011 | Hyde et al. |
| 2011/0060215 A1 | 3/2011 | Tupin, Jr. et al. |
| 2011/0087113 A1 | 4/2011 | Mack et al. |
| 2011/0105853 A1 | 5/2011 | Rakowski et al. |
| 2011/0105862 A1 | 5/2011 | Gies et al. |
| 2011/0106627 A1 | 5/2011 | LeBoeuf et al. |
| 2011/0129131 A1 | 6/2011 | Avinash et al. |
| 2011/0139088 A1 | 6/2011 | Gordon |
| 2011/0160548 A1 | 6/2011 | Forster |
| 2011/0190595 A1 | 8/2011 | Bennett et al. |
| 2011/0201898 A1 | 8/2011 | Benco et al. |
| 2011/0201904 A1 | 8/2011 | Cusimano Reaston et al. |
| 2011/0205069 A1 | 8/2011 | Liu |
| 2011/0215935 A1 | 9/2011 | Zehavi |
| 2011/0218450 A1 | 9/2011 | Haefner et al. |
| 2011/0224503 A1 | 9/2011 | Cusimano Reaston et al. |
| 2011/0237906 A1 | 9/2011 | Kabakov |
| 2011/0251469 A1 | 10/2011 | Varadan |
| 2011/0298619 A1 | 12/2011 | O'Hare et al. |
| 2012/0009943 A1 | 1/2012 | Greenberg |
| 2012/0029345 A1 | 2/2012 | Mahfouz et al. |
| 2012/0029359 A1 | 2/2012 | Sterzer et al. |
| 2012/0050046 A1 | 3/2012 | Satorius |
| 2012/0059235 A1 | 3/2012 | Davies |
| 2012/0068848 A1 | 3/2012 | Campbell et al. |
| 2012/0078127 A1 | 3/2012 | McDonald et al. |
| 2012/0089492 A1 | 4/2012 | Scalisi et al. |
| 2012/0119905 A1 | 5/2012 | Scalisi et al. |
| 2012/0122480 A1 | 5/2012 | Scalisi et al. |
| 2012/0146795 A1 | 6/2012 | Margon et al. |
| 2012/0146796 A1 | 6/2012 | Margon et al. |
| 2012/0150327 A1 | 6/2012 | Altman et al. |
| 2012/0179004 A1 | 7/2012 | Roesicke et al. |
| 2012/0179012 A1 | 7/2012 | Saffarian |
| 2012/0215077 A1 | 8/2012 | Geissler et al. |
| 2012/0242501 A1 | 9/2012 | Tran et al. |
| 2012/0245439 A1 | 9/2012 | Andre et al. |
| 2012/0245464 A1 | 9/2012 | Tran |
| 2012/0266251 A1 | 10/2012 | Birtwhistle et al. |
| 2012/0296176 A1 | 11/2012 | Herbst |
| 2012/0299731 A1 | 11/2012 | Triener |
| 2012/0316455 A1 | 12/2012 | Rahman et al. |
| 2012/0316456 A1 | 12/2012 | Rahman et al. |
| 2012/0316458 A1 | 12/2012 | Rahman et al. |
| 2012/0316471 A1 | 12/2012 | Rahman et al. |
| 2012/0330112 A1 | 12/2012 | Lamego et al. |
| 2013/0014706 A1 | 1/2013 | Menkes |
| 2013/0072765 A1 | 3/2013 | Kahn et al. |
| 2014/0182519 A1 | 7/2014 | Tupin, Jr. |

FOREIGN PATENT DOCUMENTS

| | | |
|---|---|---|
| DE | 102009040198 A1 | 3/2011 |
| EP | 1 957 999 A2 | 8/2008 |
| EP | 2 172 052 A1 | 4/2010 |
| EP | 2 255 216 A2 | 12/2010 |
| GB | 2 347 503 A | 9/2000 |
| GB | 2 387 465 A | 10/2003 |
| JP | S55-166481 U | 11/1980 |
| JP | 2003310077 A | 11/2003 |
| JP | 3099981 U | 4/2004 |
| JP | 2004-528123 A | 9/2004 |
| JP | 2005102959 A | 4/2005 |

(56) References Cited

FOREIGN PATENT DOCUMENTS

| | | |
|---|---|---|
| JP | 2005170370 A | 6/2005 |
| JP | 2007-236251 A | 9/2007 |
| JP | 2008-526388 A | 7/2008 |
| JP | 2009178142 A | 8/2009 |
| JP | 2009-219867 A | 10/2009 |
| JP | 2011-103812 A | 6/2011 |
| JP | 2011-142866 A | 7/2011 |
| JP | 2012-045373 A | 3/2012 |
| JP | 2012-146029 A | 8/2012 |
| KR | 2003-0061157 A | 7/2003 |
| WO | 87/006113 A1 | 10/1987 |
| WO | 02/056274 A1 | 7/2002 |
| WO | 03/023439 A2 | 3/2003 |
| WO | 03/025826 A2 | 3/2003 |
| WO | 2005/041131 A2 | 5/2005 |
| WO | 2005/058192 A2 | 6/2005 |
| WO | 2005/104930 A1 | 11/2005 |
| WO | 2007/062244 A2 | 5/2007 |
| WO | 2008057883 A2 | 5/2008 |
| WO | 2008/104810 A1 | 9/2008 |
| WO | 2008/148051 A1 | 12/2008 |
| WO | 2009/061328 A1 | 5/2009 |
| WO | 2009/088688 A2 | 7/2009 |
| WO | 2009/105243 A2 | 8/2009 |
| WO | 2009/106896 A2 | 9/2009 |
| WO | 2010/019307 A1 | 2/2010 |
| WO | 2010/118173 A2 | 10/2010 |
| WO | 2011149565 A1 | 12/2011 |
| WO | 2012140547 A1 | 10/2012 |
| WO | 2012146957 A1 | 11/2012 |
| WO | 2013118121 A1 | 8/2013 |

OTHER PUBLICATIONS

Feb. 22, 2019—(NZ) Examination Report—App 734823.
Sep. 2, 2015 (US)—Office Action—U.S. Appl. No. 14/286,361.
Aug. 24, 2018—(CA) Office Action—App 2,907,170.
Feb. 5, 2018 (AU) Examination Report—App 2017202246.
Feb. 1, 2019—(AU) Notice of Acceptance—App 2017202246.
Jun. 25, 2014—PCT/U.S. International Search Report and Written Opinion—App 2014/022257.
Sep. 16, 2014—PCT/U.S. International Search Report and Written Opinion—App 2014/022273.
Oct. 9, 2014—PCT/U.S. International Search Report and Written Opinion—App 2014/037518.
Sep. 24, 2015—U.S. Final Office Action—U.S. Appl. No. 13/840,298.
Aug. 26, 2015—U.S. Non-Final Office Action—U.S. Appl. No. 13/838,988.
Mar. 11, 2015—U.S. Non-Final Office Action—U.S. Appl. No. 13/840,298.
Dec. 4, 2015—U.S. Non-Final Office Action—U.S. Appl. No. 14/086,721.
Dec. 16, 2015—(NZ) First Examination Report—App 712541.
Apr. 5, 2016—(AU) Patent Examination Report No. 1—App 2014237545.
Sep. 24, 2015—PCT/U.S. International Preliminary Report on Patentability—App 2014/022273.
Sep. 15, 2015—PCT/U.S. International Preliminary Report on Patentability—App 2014/022257.
May 2, 2016—U.S. Final Office Action—U.S. Appl. No. 13/838,988.
May 12, 2016—U.S. Non-Final Office Action—U.S. Appl. No. 13/840,298.
May 23, 2016—(NZ) Examination Report—App. 712541.
Jun. 6, 2016—(KR) Office Action—App 10-2015-7029908.
Aug. 9, 2016—(JP) Office Action—App. 2016-500935.
Sep. 28, 2016—(CA) Office Action—App. 2,907,170.
Sep. 30, 2016—(AU) Patent Examination Report No. 1—App. 2014237542.
Oct. 20, 2016—(KR) Office Action—App. 10-2015-7029903.
Nov. 4, 2016—(NZ) Further Examination Report—App. 712541.
Nov. 15, 2016—(JP)—Notification of Reasons for Refusal—App. 2016-500929.
Nov. 29, 2016—U.S. Final Office Action—U.S. Appl. No. 13/840,298.
Dec. 20, 2016—(AU) Examination Report No. 1—App. 2014353503.
Dec. 8, 2016—(CA) Office Aciton—App. 2,907,167.
Taoufik et al., The Ultra Wide Band Radar System Parameters in Medical Application, Journal of Electromagnetic Analysis and Applications, 2011, 3, 147-154.
Apr. 24, 2017—(NZ) Further Examination Report—App. 719948.
Jun. 1, 2017—(CN) Office Action—App. 201480063728.7.
Mar. 3, 2017—(CA) Office Action—App. 2,930,264.
Jul. 11, 2017—(JP) Office Action—App. 2016-529969.
Oct. 13, 2017—U.S. Office Action—U.S. Appl. No. 13/838,988.
Nov. 1, 2017—(CN) Second Office Action—App 201480027974.7—Eng Tran.
Jan. 18, 2018—(EP)—Search Report—App 14733000.5.
Jun. 15, 2018—(NZ) First Examination Report—App 734823.
Aug. 1, 2018—(MX) Office Action—App 15/12856.
Oct. 17, 2018—(EP) Examination Report—App 14716099.8.
Oct. 17, 2018—(EP) Office Action—App 14716099.8.
Dec. 3, 2018—(AU) Examination Report—App 2018202255.
Jan. 9, 2019—(EP) Intention to Grant—App 14733000.5.

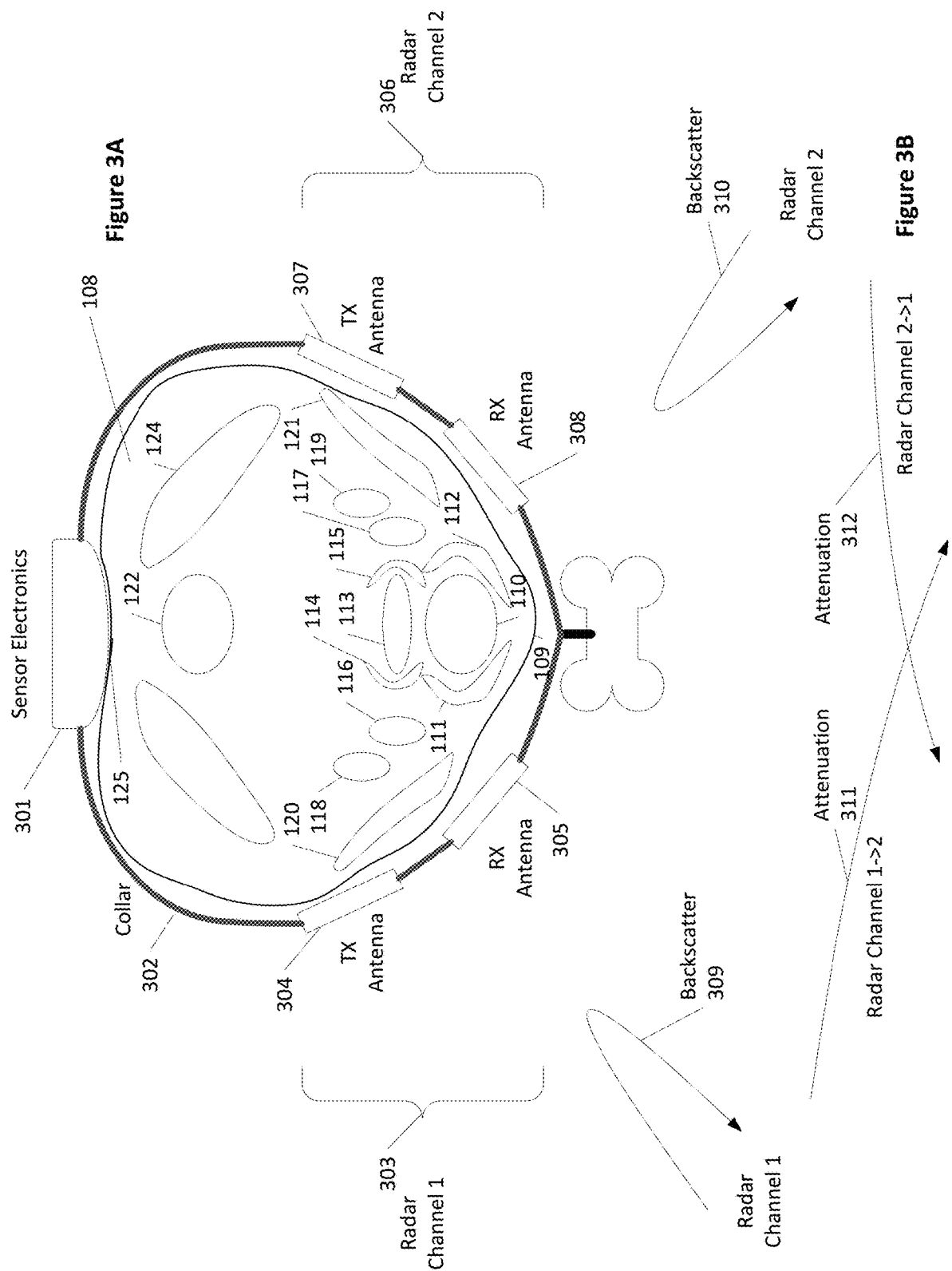

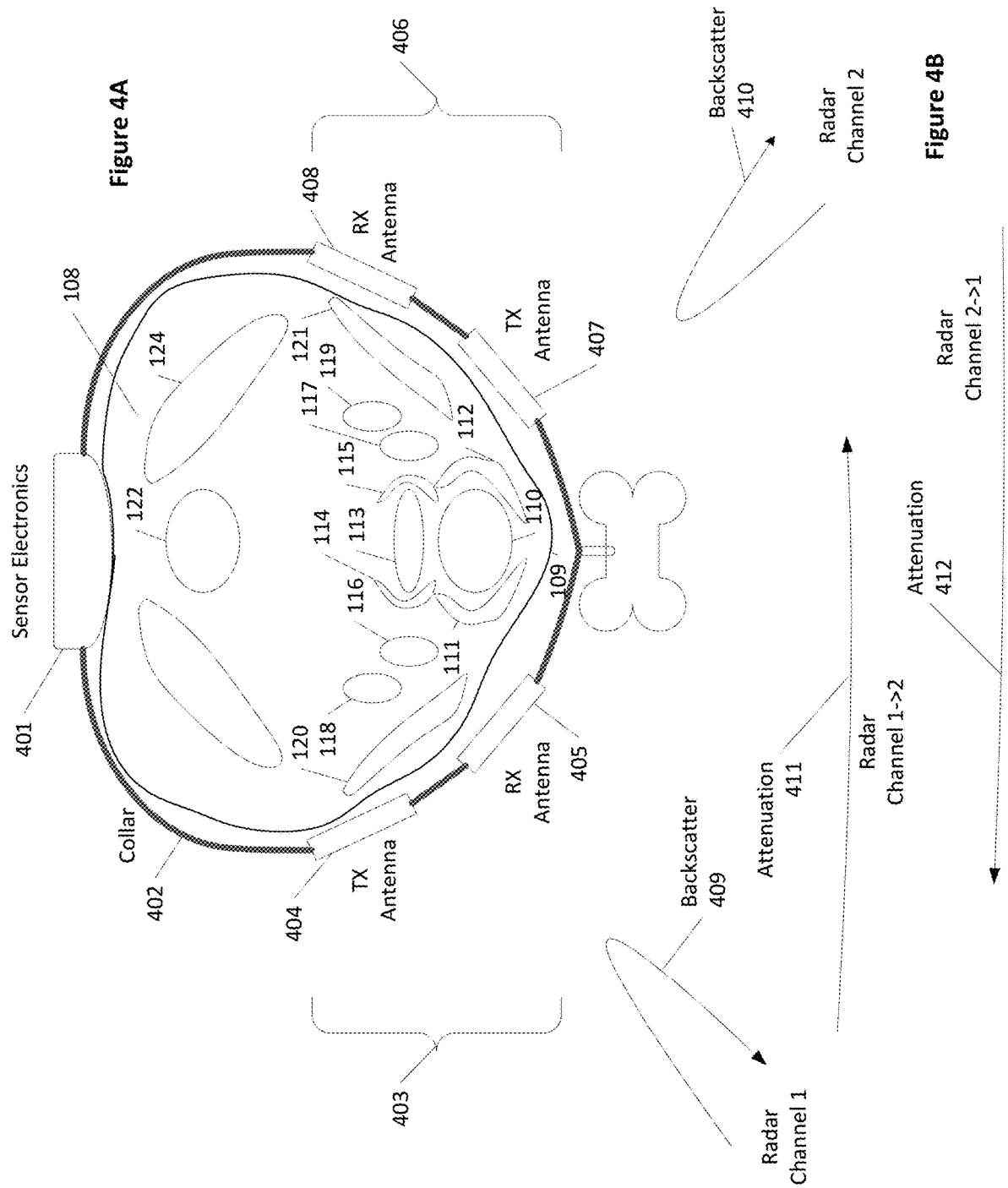

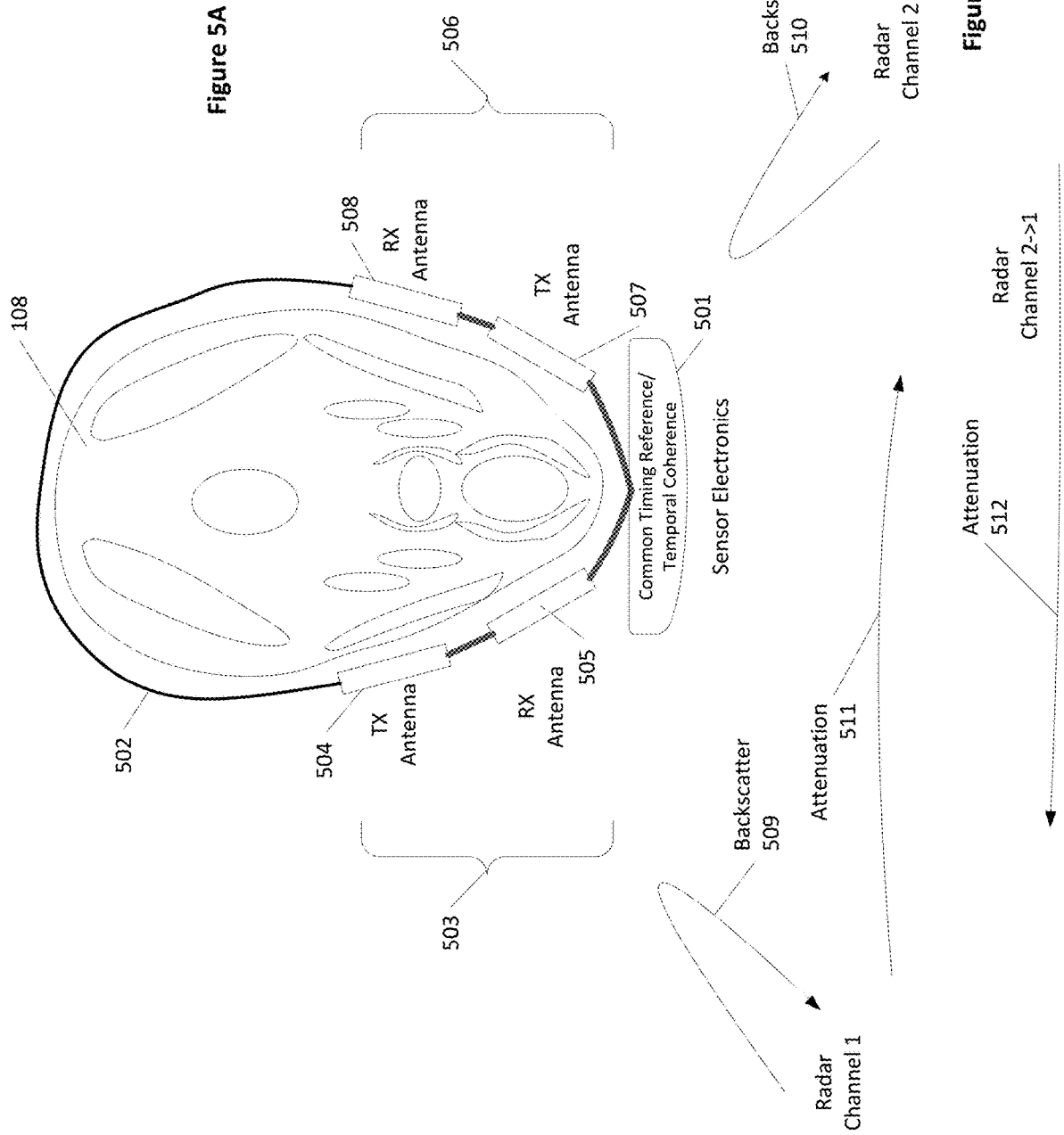

ANIMAL HEALTH AND WELLNESS MONITORING USING UWB RADAR

RELATED APPLICATION INFORMATION

This application is a continuation of U.S. application Ser. No. 15/377,281, filed Dec. 13, 2016, which claims priority to U.S. application Ser. No. 14/086,721, filed Nov. 21, 2013, now U.S. Pat. No. 9,526,437, which claims priority benefit of U.S. Application No. 61/729,298, filed Nov. 21, 2012, all of which are incorporated herein by reference in their entirety.

BACKGROUND

1. Technical Field

Aspects of this disclosure relate to the use of radar in monitoring physiological conditions of mammals.

2. Related Art

Animals, like humans, can suffer from injury or illness, negatively impacting their health. Timely detection of changes in health through either regular or event driven episodic monitoring of physiological processes can enable veterinary intervention, potentially reducing the effects of an adverse condition, improving the quality of life, and prolonging life. In particular, cardiac and respiratory monitoring provides useful information on the health of an animal and these types of information are commonly used to diagnose, treat, and manage the animal.

Animals can represent a large financial and often, emotional investment. Health monitoring can help optimize veterinary care to protect that investment and provide peace of mind to the owner. Monitoring is applicable to a wide range of animals, including feed stock, breeding stock, exotic/endangered species, animal athletes, performing animals, and domestic pets. Monitoring can be accomplished whether the animal is in the wild, in captivity (e.g., a zoo or animal park), in a pasture or free-range, in a barn or stable, at home or in the yard, in a pen or a crate.

Animal health monitoring is challenging. Many familiar sensor technologies—e.g., electrocardiogram (ECG), pulse oxygen, ultrasound, and temperature, require direct skin contact, making them impractical for use with animals having fur or feathers. They may also require that the sensor be positioned on a specific location on the body which again may be impractical. For example, assuming prior removal of the fur, pulse ox sensors typically need to be placed on thin anatomical structures such as ears, making them prone to loss through scratching, rubbing, or shaking. Similarly, ECG sensors are usually placed on the torso, in proximity to the heart and the Einthoven triangle, making them prone to loss through scratching, rubbing, or shaking. Finally, there is no sensor currently available that is capable of providing a direct, unobtrusive measurement of respiration—a needed metric in understanding and managing animal health.

The monitoring of respiration is currently under-appreciated in veterinary care and there are only a handful of researchers in the country studying/teaching animal pulmonology. This lack of integration into veterinary medicine is in contrast to the body of published information dating back several decades concerning the role of respiratory symptoms in the diagnosis and treatment of animal cardiac and respiratory disease. One of the obstacles in integrating respiratory monitoring into veterinary practice is the lack of appropriate non-invasive sensors. Most veterinarians are forced to rely on manual observations—watching the animal, to obtain respiratory data. These observations are of limited use and complicated by the visit to the vet as this usually leads to animal anxiety and elevated cardiopulmonary functions that are not representative of the animal's true underlying health. Respiratory monitoring is not viewed as an important parameter because of the difficulty in obtaining accurate data.

Respiratory monitoring in the animal's nature environment—e.g., at home for a pet or in a pasture for a horse or cow, would be a benefit to veterinary medicine as the data would be more representative of the animal's actual state of health. This data could be used to help treat animals with known medical problems as well as identify animals that may be developing medical problems. There are a number of medical problems that exhibit respiratory symptoms, including heart disease, heart murmur, pulmonary edema, pulmonary fibrosis, sleep apnea, COPD, asthma, larynx paralysis, kennel cough (bordetella), and others. Specific to domestic pets, respiratory monitoring would be important with brachycephalic dogs—breeds with short muzzles such as bulldogs, cavaliers, pugs, Boston terriers, Boxers, Pekingese, shih tzu, etc. These breeds have a high incidence of respiratory problems and are inefficient "panters", leading to inflamed respiratory tracts and laryngeal problems as well as making them much more susceptible to heat stroke. Timely identification of respiratory distress would enable earlier and less complicated/expensive intervention and reduce the risk to the animal.

As discussed above, many medical monitoring technologies are impractical or unusable with animals. Doppler radar approaches, whether CW or pulsed, have been investigated as a technique for collecting cardiopulmonary data. They have generally relied on off-body or non-contact monitoring where the Doppler radar sensor is separated from the subject by an air gap and thus, does not make direct contact with the patient. Due to the large difference between the relative dielectric properties of the primary propagation medium (air, where $\varepsilon_r=1$) and living tissue ($\varepsilon_r \approx 50$), most of the RF energy is reflected at the skin surface with little energy propagating into the interior of the body to interrogate the internal organs. Any energy that does propagate into the torso and is subsequently reflected by the internal organs is greatly reduced by internal tissue absorption as well as a second transition across the skin-air boundary, resulting in little energy from the anatomical target making it back to the receiver. Low returns equate to marginal data.

A common technique for isolating a specific physiological process involves combining Doppler with auto-correlation. Auto-correlation samples the time-domain waveform and correlates the Nth pulse with a period of time after the Nth pulse where the period is centered on the anticipated rate of the specific physiological process under review based on the Doppler results. High correlation coefficients equate to greater confidence that the system has locked onto the specific physiological process. An externally defined threshold is often used to determine adequate correlations and thus, sufficient target acquisition.

Because of the strong surface component associated with respiration (typically 1 cm chest wall displacement in an average adult male), off-body techniques can collect reasonable pulmonary data but those physiological processes that do not have strong surface components, such as cardiac activity, are difficult to detect and measure with Doppler. Another limitation of Doppler is its general inability to distinguish motion associated with more than one physiological process when those processes operate at similar rates. For example, in subjects experiencing bradycardia, the cardiac rate will approach and sometime drop below the respiratory rate, making it difficult for Doppler to distinguish the two processes from each other.

SUMMARY

Once or more aspects relate to a collar with an ultra-wideband radar. A housing contains sensor electronics and the transmit and receive antennas are located separate from the housing around the circumference of the collar. A first example of the collar includes a first transmit antenna and a first receive antenna. A second example of the collar adds a second transmit antenna and a second receive antenna. The antennas may be positioned to obtain position and movement information from various internal structures including a carotid artery, a jugular vein, and muscles surrounding an esophagus and trachea.

BRIEF DESCRIPTION OF DRAWINGS

FIG. 3A is a first illustrative example of a multistatic radar on the neck of an animal in accordance with one or more embodiments. FIG. 3B shows signal paths for the multistatic radar of FIG. 3A.

FIG. 4A is a second illustrative example of a multistatic radar on the neck of an animal in accordance with one or more embodiments. FIG. 4B shows signal paths for the multistatic radar of FIG. 4A.

FIG. 5A shows an illustrative example of a multistatic radar on a narrow neck of an animal in accordance with one or more embodiments. FIG. 5B shows signal paths for the multistatic radar of FIG. 5A.

DETAILED DESCRIPTION

The following description relates to configurations of ultra-wideband (UWB) sensors for obtaining physiological information from mammals. Specifically, aspects of the disclosure pertain to the use of UWB sensors as medical radar to the extent they use very low power Ultra Wide Band (UWB) radio frequency (RF) energy. In practice, the UWB medical radar emits a narrow pulse of electromagnetic energy, which propagates into a body. As the energy enters the body, small amounts of the incident energy are reflected back to the device. The reflections are due to the differences in dielectric properties of the illuminated tissues and organs. The reflected energy is then received and processed using application-specific signal processing algorithms to extract information on the type, location, size, and motion of the illuminated tissues and organs. It is appreciated that the greater the dielectric constant between illuminated tissues and organs increases the reflection (or backscatter) of the electromagnetic pulse.

Examples of UWB medical radar systems are found, for instance, in U.S. Pat. No. 7,725,150 to Tupin, Jr. et al. and U.S. Pat. No. 8,463,361 to Tupin, Jr., both assigned to LifeWave, Inc. of Los Altos, Calif., whose contents are expressly incorporated by reference to their entirety.

Ultra-wideband radar overcomes one of the limitations found with Doppler radar because of the extremely fine radial resolution (<5 mm) inherent with UWB radar, allowing the UWB sensor to more easily isolate different physiological processes based on their unique locations within the patient. The sensor can focus on one or more depths using traditional range sweep techniques and, if the sensor is configured as an array, further focal processing techniques based on beam-steering and beam-forming can be applied.

A contact-based UWB medical sensor for monitoring the health of animals has several distinct advantages over Doppler and off-body monitoring. The UWB radar does not need direct skin contact or coupling gels, allowing it to collect useful physiological data through fur or feathers yet by maintaining contact with fur or feathers. As such, the large reflective losses associated with the skin-air interface are significantly reduced. Second, assuming the electronics are sufficiently protected from the environment (e.g., sealed against rain and moisture or otherwise moisture resistant), the radar may operate when wet or dirty.

Figure 1:
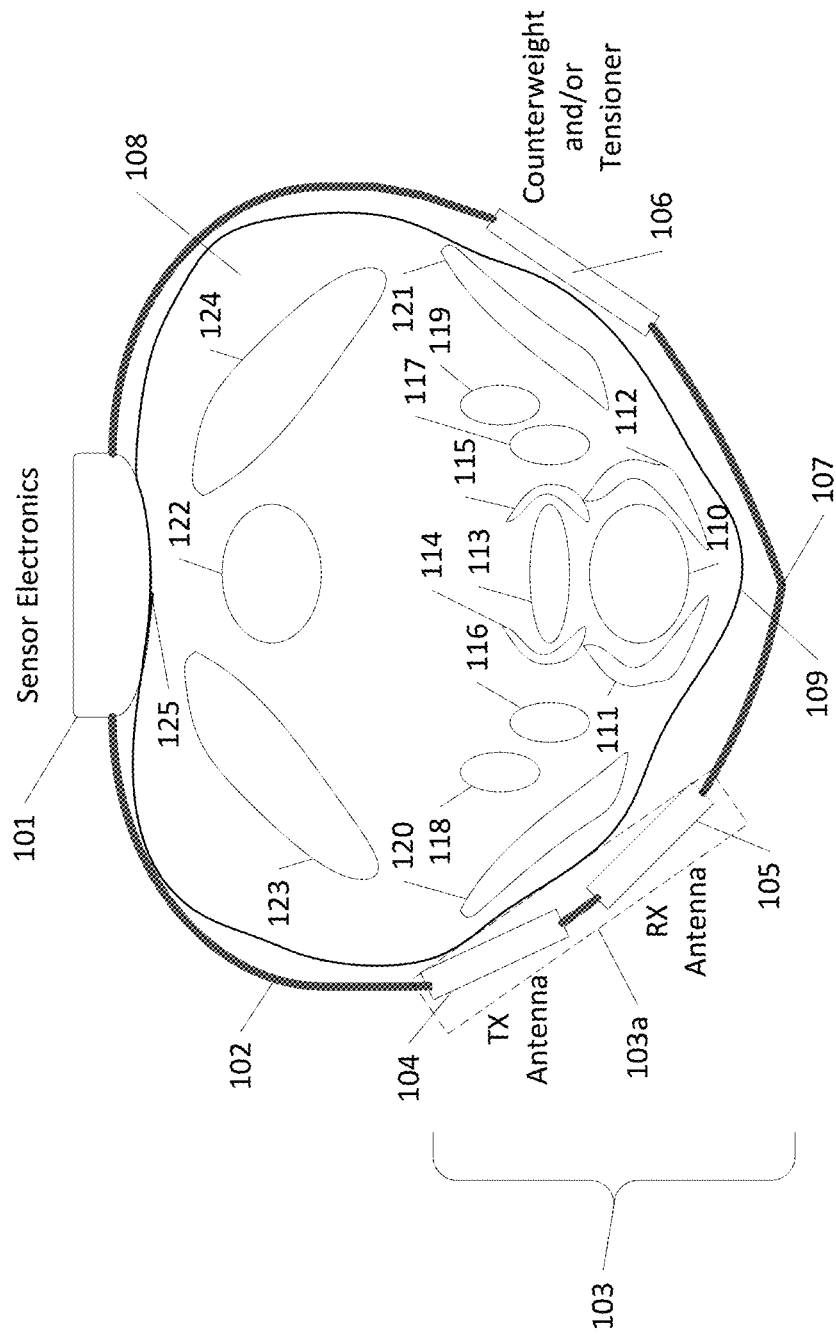
FIG. 1 is an illustrative example of a monostatic radar on the neck of an animal in accordance with one or more embodiments.

For instance, a UWB radar system may be placed on an animal's collar as shown in FIG. 1. FIG. 1 shows a cross-sectional view of an animal's neck and the collar being worn by the animal. The UWB radar system of FIG. 1 includes sensor electronics 101 in a housing and antennas 103 including a transmit antenna 104 and a receive antenna 105. The antennas 104 and 105 may be placed together in a singular housing 103a or may be housed separately. One advantage of housing the antennas 104 and 105 together is that the direction each antenna faces may be fixed with respect to the other antenna.

These components of the UWB radar system may be co-located at a single location or may be placed around the collar 102 as shown in FIG. 1 and connected by wires, cables, traces on a circuit board (rigid or flexible), or other known electrical connecting techniques. If co-located, an example of a size of the combination of the antennas 104 and 105 and the sensor electronics 101 may be 7.4 cm×2.3 cm×1.8 cm and weigh 29 g.

The UWB radar system monitors movement of different structures based on their different dielectric constants relative to surrounding structures or tissues. The change in location of the interfaces between these structures is monitored by the UWB radar system and is subsequently analyzed through known analysis techniques of UWB radar signals.

Aspects of this disclosure relate to configurations of the UWB radar system to provide improved signals for analysis. For reference, FIG. 1 shows the animal's neck 108 with skin 109, trachea 110 with surrounding muscles 111, 112, esophagus 113 with surrounding muscles 114, 115, carotid arteries 116, 117, jugular veins 118, 119, spinal column 122, and various other muscles (including lower muscle groups 120, 121, and upper muscle groups 123 and 124).

In one example, the UWB radar system with sensor electronics 101 and antennas 103 may be co-located (namely, the sensor electronics 101 module being positioned radially outward from antennas 103 relative to neck 109) as a monostatic radar structure and hang off collar at a bottommost position 107 relative to the animal's neck 108, closest to the trachea 110.

In another example, as shown in the configuration of FIG. 1, sensor electronics 101 are positioned at the top of the neck 108 with the antennas 103 located on the side of neck 108, also as a monostatic radar structure. Here, by placing transmit antenna 104 and receive antenna 105 closer to carotid artery 116 and jugular vein 118, the beam from the transmit antenna 104 and returning to receive antenna 105 may encounter fewer dialectically different structures when located at the position shown in FIG. 1 then when located at position 107. This reduction in the number of dialectically different structures reduces backscatter signals from those different structures.

As depicted, collar 102 may include a counterweight 106 that may be approximately the weight of antennas 103 balance the UWB radar system and attempt to maintain antennas 103 at their side placement around the neck 108.

Alternatively or in addition to counterweight 106, a tensioner may be used to maintain a relatively constant tension on collar 102 to help position antennas 103 on the side of the neck 108.

Further, as larger animals have stronger neck muscles (for instance muscles 123, 124), these muscles in some instances may form a recess 125 upward of spinal column 122. The inside shape of sensor electronics 101 may be convex to allow at least some nestling in the concave recess formed by muscle groups 123 and 124.

By placing antennas 103 and aside position as shown in FIG. 1, accurate readings from the animal's carotid artery 116 and/or jugular vein 118 may be obtained. Depending on the type of animal, the antennas 103 may be angled relative to neck 108 and/or to each other to allow for illumination of relevant structures and collection of backscattered signals from those structures. For instance, to concentrate solely on carotid artery 116, the receive antenna 105 may be moved closer to transmit antenna 104 to receive the stronger backscatter signals roughly in line with the radiated beam from transmit antenna 104 plan. Alternatively, to concentrate on carotid artery 116 and the movement of muscles 114 and 115 surrounding esophagus 113, receive antenna 105 may be moved farther away from transmit antenna 104. Further, to also include signals from the movement of muscles 111 and 112 surrounding trachea 110, the receive antenna 105 may be moved further from transmit antenna 104. In these examples, the various muscle groups may be monitored surrounding the trachea 110 as the trachea's cartilage may not reflect the UWB pulses and the movement of the cartilage is not detectable directly.

In many applications across a range of species, the UWB radar sensor can be placed within or on a collar or harness where the choice of the garment and specific sensor placement upon or within the garment is driven by the desired medical data, the need to locate the sensor in the proximity of the key primary and alternative secondary anatomical structures required to obtain the desired data, and the need to secure the sensor to the animal such that it is unlikely to be dislodged or removed during normal activity. In addition, the shape of the sensor and its antennas can be modified to take advantage of the anatomy to assist with placement and maintain position.

Actual signal processing and display of results does not have to be co-located with the sensor and in fact, remote processing and display might be highly desirable. The data can be processed (partially or completely) locally using an embedded processor (for instance, microcontroller or discrete signal processor) or wirelessly transferred to another processing platform—dedicated base station, smart phone, tablet, PC, or the cloud using a conventional wireless transfer system (transmitter in the sensor electronics 101 to transmit a signal to of receiver over, for instance a Wi-Fi connection). The display can be a digital readout on a panel built into the base station or take advantage of the GUI capabilities of any number of consumer electronics.

Of the various limitations described herein, a collar 102 allows collection of basic cardiopulmonary data without the need to be directly over the heart and lungs. The collar with its UWB radar system collects data primarily from the carotid arteries in the neck, as well as physiological data associated with motion of the larynx, trachea, and esophagus. Data from these structures enables monitoring of consumption—e.g., food and water, vomiting and regurgitation, as well as enabling the detection of choking and vocalization—e.g., barking, or other processes involving the larynx and trachea based on analyses of received signals including identification of the frequency components of the signals, the magnitude of those frequency components, and how those signals change over time. Other sensor technologies may be added to the assembly to support data fusion for improved accuracy, reliability, and noise reduction.

Further, an additional counterweight (e.g., the animal's tag or other collar attachment) may be provided at location 107 to provide a weight that may further aid in aligning the sensor electronics 101 and antennas 103.

Figure 2:
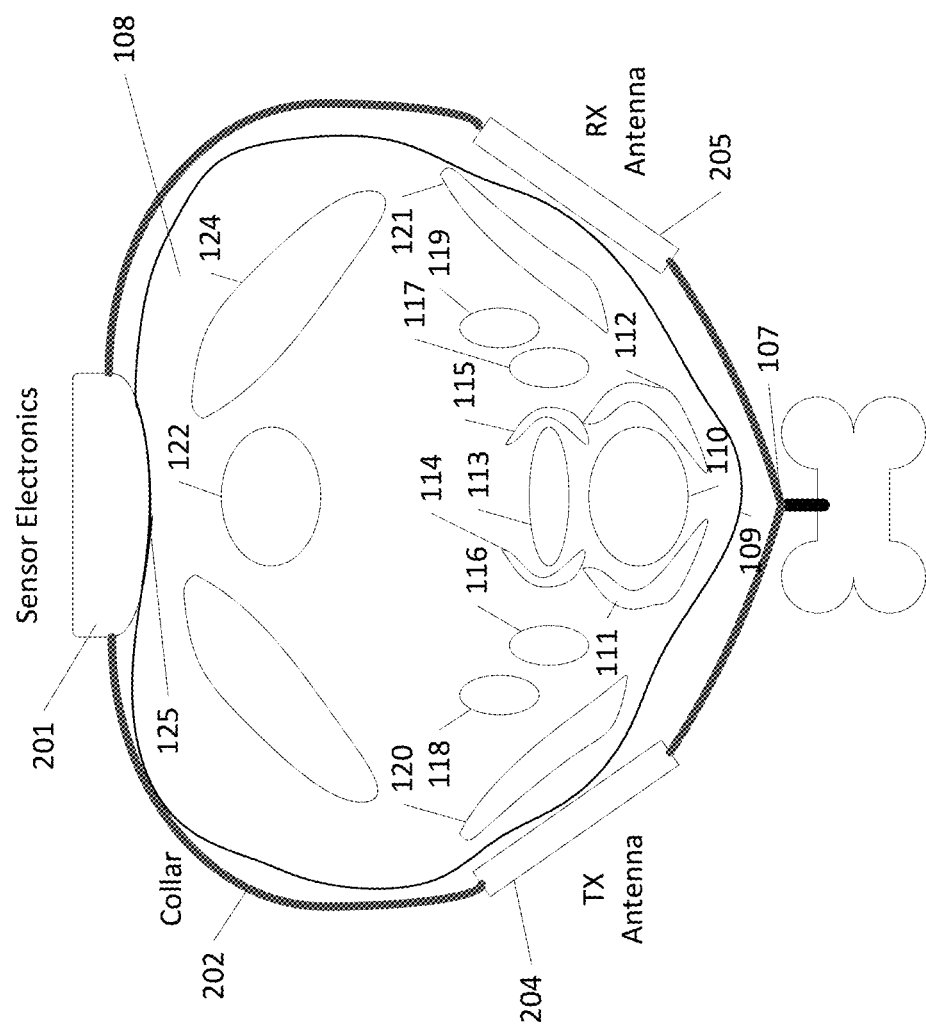
FIG. 2 is an illustrative example of a bistatic radar on the neck of an animal in accordance with one or more embodiments.

FIG. 2 shows another configuration of sensor electronics 201 and the antennas. In FIG. 2, transmit antenna 204 is located on a first side of neck 108 and receive antenna 205 is located on a symmetrically opposite side of neck 108. Here, the antennas 204 and 205 may be symmetrically distributed around the circumference of the neck 108 to maintain an even weight distribution on collar 202. One example of this configuration would have the sensor electronics 101 in the depression over the spinous process 125—see FIGS. 1 and 2, enabling easy and consistent placement of the sensor electronics 201. Unlike the anterior of the neck where many animals have a wattle and are sensitive to any object, this location typically has less fat tissue, less loose skin, and has less anatomical variation within a specific species or breed.

The configuration of transmit antenna 204 being separate from receive antenna 205 FIG. 2 is commonly referred to as a bistatic radar architecture. In the minimal separation case, both the TX and RX antennas may be located along the spine while in the limit, they could be located on either side of the larynx.

In FIG. 2, the receive antenna 205 may receive backscatter from some structures inside neck 108. For structures that have a strong dielectric difference from surrounding structures, the amplitude of the backscatter signals may predominate the received collection of signals. However for structures that have a less significant dielectric difference from surrounding structures, the resultant backscatter from these less significant dielectric differences is weaker. Thus, when attempting to monitor movement of different structures relative to each other where the dielectric constants of these structures are relatively close to one another, monitoring backscatter signals is more difficult. In this situation, monitoring signal modification (signal amplification, attenuation, polarization, retardation or advancement, and the like) with a receive antenna 205 generally facing transmit antenna 204 is preferable.

The above bistatic of FIG. 2, configuration could be expanded to a multistatic configuration with a corresponding increase in weight, cost of goods, and power consumption. As shown in FIG. 3A, the sensor may include two radar channels 303 and 306, each consisting of a TX and RX pair (304/305 and 307/308, respectively), where one radar channel interrogates the right side of the neck and one radar channel interrogates the left side.

This configuration takes advantage of the symmetry in the neck to improve signal reception while reducing common noise. More radar channels may be added for additional performance improvements.

As shown in FIG. 3B, radar channel 1 303 is shown on the left side of FIG. 3A and radar channel 2 306 is shown on the right side of FIG. 3A. The backscatter signal 309 of radar channel 1 303 from transmit antenna 304 enters and then returns back through the side of neck 108 to receive antenna 305. Similarly, the backscatter signal 310 of radar channel 2 306 from transmit antenna 307 enters and then returns back through side 306 of neck 108 to receive antenna 308. Also, receive antenna 308 receives attenuation signal 311 (from radar channel 1 to radar channel 2) as originally transmitted from transmit antenna 304. Likewise, receive antenna 305 receives attenuation signal 312 (from radar channel 2 to radar channel 1) as originally transmitted from transmit antenna 307.

To permit attenuation signals 311 and 312 to be received and used by sensor electronics 301, common timing signals used to control the transmission of the UWB pulses in the multistatic UWB radar system are used in radar channel 1 and radar channel 2. For instance, when transmit antenna 304 has finished transmitting, both receive antenna 305 and receive antenna 308 may both be active (in accordance with the same or a temporally adjusted timing signal) in receiving signals scattered and/or modified by the combination of various structures in neck 108. Alternatively, transmit antenna 304 and transmit antenna 307 may transmit simultaneously in accordance with the same or temporally adjusted timing signal with one of receive antenna 305 or receive antenna 308 also being active (and likewise being responsive to the same or temporally adjusted timing signal). Finally, transmit antenna 304 and transmit antenna 307 may both transmit simultaneously and receive antenna 305 and receive antenna 308 may both receive signals simultaneously with all operations coordinated through the same or temporally adjusted timing signal. The purpose using the same or temporally adjusted timing signal in sensor electronics 301 is to provide temporal coherence for the operations of radar channel 1 303 and radar channel 2 306.

FIG. 4A shows a similar structure to that of FIG. 3A in which sensor electronics 401 controls radar channel 1 403 (with transmit antenna 404 and receive antenna 405) and greater channel 2 406 (with transmit antenna 407 and receive antenna 408). Here, the locations of the transmit antenna and receive antenna of radar channel 2 406 are flipped relative to the locations of transmit antenna 404 and receive antenna 405. While backscatter signal 409 of radar channel 1 is similar to that shown in FIG. 3B, backscatter signal 410 is reflected more upwards then backscatter signal 310 of FIG. 3B (which is reflected more downwards). Also, attenuation signal 411 from transmit antenna 404 to receive antenna 408 is generally more horizontal than attenuation signal 311. Similarly, attenuation signal 412 from transmit antenna 4072 receive antenna 405 is also generally more horizontal than attenuation signal 412.

As with the sensor electronics 301 of FIG. 3A, sensor electronics 401 of FIG. 4A may also use temporally coherent timing signals to allow the multistatic operation of the transmit and receive antenna components of FIG. 4A.

FIG. 5A shows a configuration similar to that of FIG. 4A but with an animal having a narrower neck 108. FIG. 5A shows collar 502, sensor electronics 501 (with the common timing reference providing temporal coherence among radar channel 1 503 and radar channel 2 506), transmit antennas 504 and 507, receive antennas 505 and 508. FIG. 5B shows backscatter signals 509 and 510 and attenuation signals 511 and 512.

In all cases (including monstatic, bistatic, and multistatic), the location, orientation, and antenna characteristics of the paired TX and RX antennas for each radar channel may be designed to allow convergence of the TX and RX antenna bore sights onto the anatomical structure of interest while maintaining sufficient beamwidth at the structure of interest.

As described above, a counterweight may be integrated to minimize the potential for collar rotation while a tensioning device (springs or clips or elastically deformable materials) may be added to maintain constant pressure against the animal's neck 108, minimizing the noise caused by motion at the sensor/skin interface. Also, it is important to note that the sensor electronics and antennas do not need to be co-located as the electronics can connect to the antennas via cables or flexible circuit boards. Either of these connection techniques can be embedded into the collar itself as long as the connecting media is relatively homogeneous to minimize RF reflections.

A harness—e.g., a modified walking harness, has the advantage of allowing one or more radars to interrogate various anatomical regions of interest or to enable more sophisticated signal processing by isolating on a particular organ. For example, if the UWB radar sensor has at least one channel proximal to the heart, advanced cardiac biometrics can be obtained, including stroke volume, cardiac output, and changes in blood pressure. Similarly, if the UWB radar sensor has one channel proximal to main right and left nodes of the lungs, the system can check for asymmetrical breathing patterns.

The UWB radar is not limited to the torso for collecting cardiopulmonary data as there are many alternative locations on the animal that can be exploited, particularly for obtaining cardiac data. For example, good quality cardiac data can be collected by positioning the UWB sensor in proximity of the carotid arteries to take advantage of the expansion and contraction in the radius of the arteries throughout the cardiac cycle. In addition, positioning the sensor on the neck has been shown to provide reasonable and quantifiable respiratory information.

Various porcine animal models (weights between 30-50 kg) have been studied thank you to develop new human cardiopulmonary monitoring systems. In these studies, a UWB radar sensor was placed to the left of the animal's sternum, proximal to the heart and collected cardiopulmonary data in parallel with other reference monitors. Data from the UWB radar sensor was processed with proprietary signal processing algorithms and the results correlated against the data from the reference monitors to determine the efficacy of the radar sensor. The UWB sensor demonstrated the ability to measure cardiac and pulmonary rate, detect changes in cardiac stroke volume, measure CPR compressions, and determine the status of the circulatory system across a variety of cardiac conditions.

Most recently, the ability of the sensor to measure cardiopulmonary rates in small animals using dogs weighing less than 10 kg as the test subjects has been studied. This ability along with the capabilities previously demonstrated and described above, enables a variety of animal monitoring applications. During the tests, the cardiac rate was manually observed to be approximately 65 BPM, while the respiration rate was manually observed to be approximately 20 BPM.

Figure 6B:
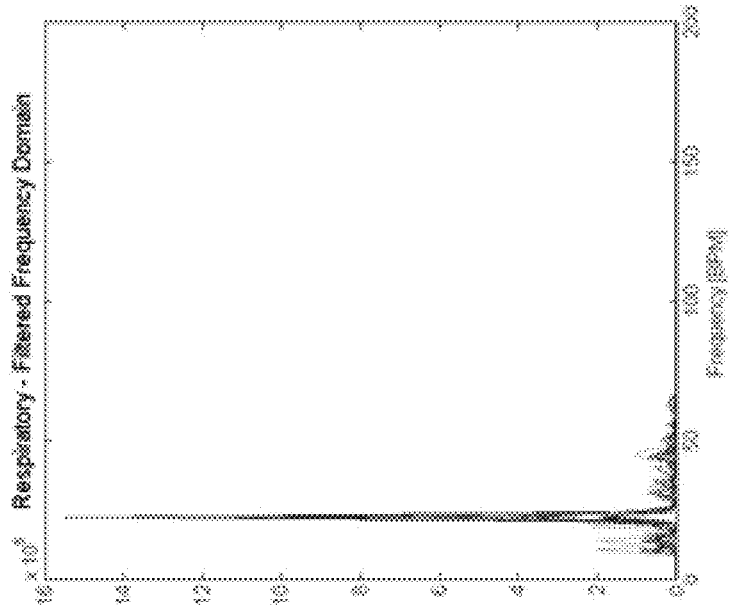
FIGS. 6A and 6B are charts showing cardiac and respiratory rates from a sternal position of a UWB sensor on an animal in accordance with one or more embodiments.
Figure 6A:
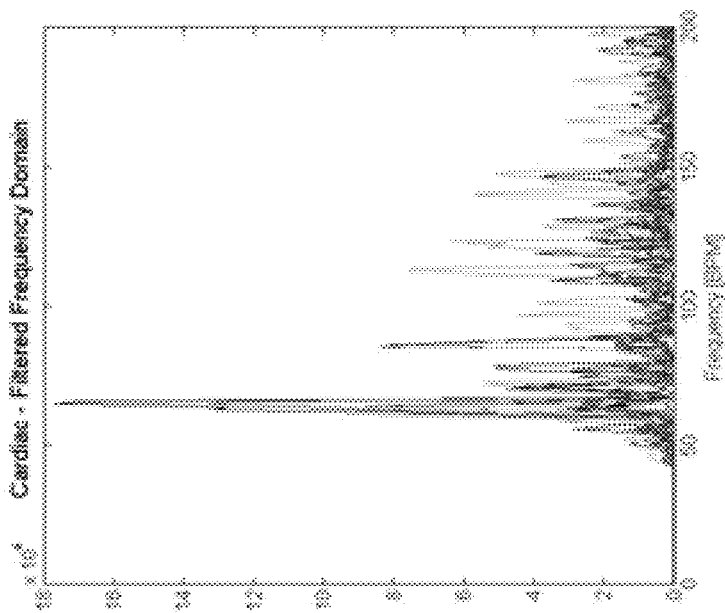

In the first test, the UWB radar sensor was placed on the left side of the animal's rib cage, approximately level with the heart while the animal was prone. As can be seen in FIGS. 6A and 6B, the cardiac rate and pulmonary rate as calculated with an FFT were readily discernible and matched manual measurements.

Figure 7B:
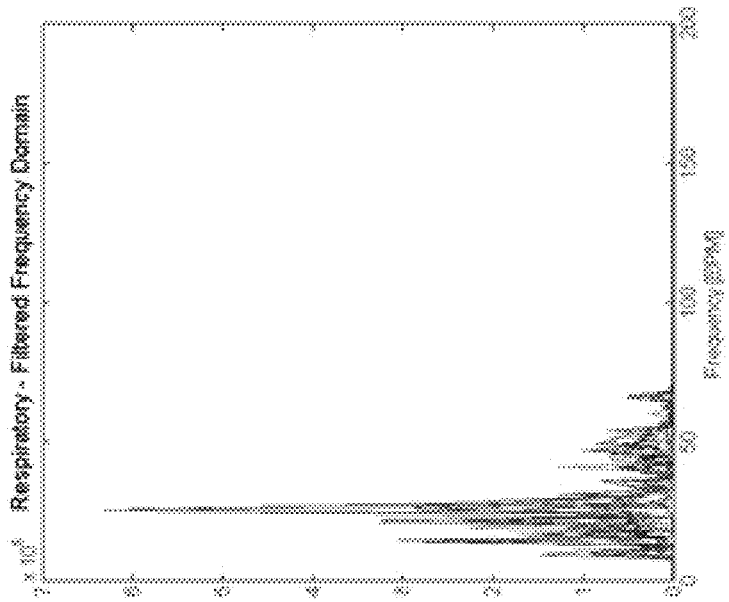
FIGS. 7A and 7B are charts showing cardiac and respiratory rates from a right carotid position of the UWB sensor.
Figure 7A:
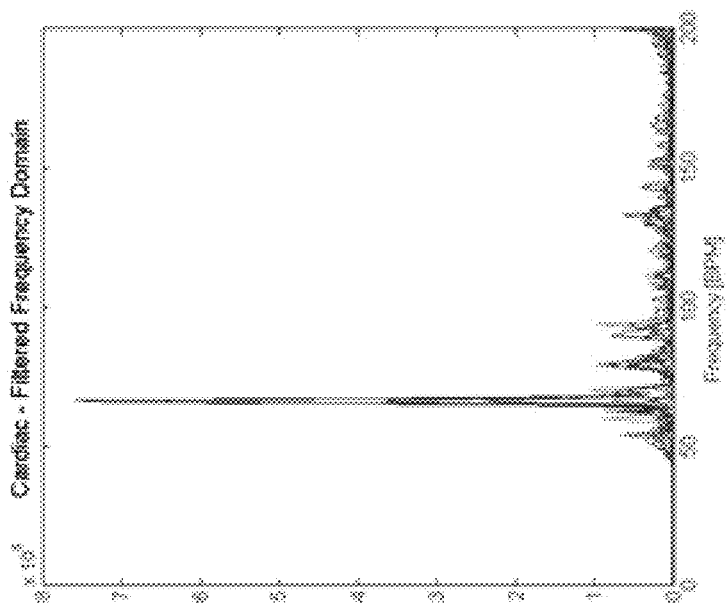

In the second test, the UWB radar sensor was placed on the right side of the animal's neck, over the carotid artery with the axis of the sensor parallel to the longitudinal axis of the artery. As can be seen in FIGS. 7A and 7B, the cardiac rate and pulmonary rate as calculated with an FFT were readily discernible and matched manual measurements.

Figure 8A:
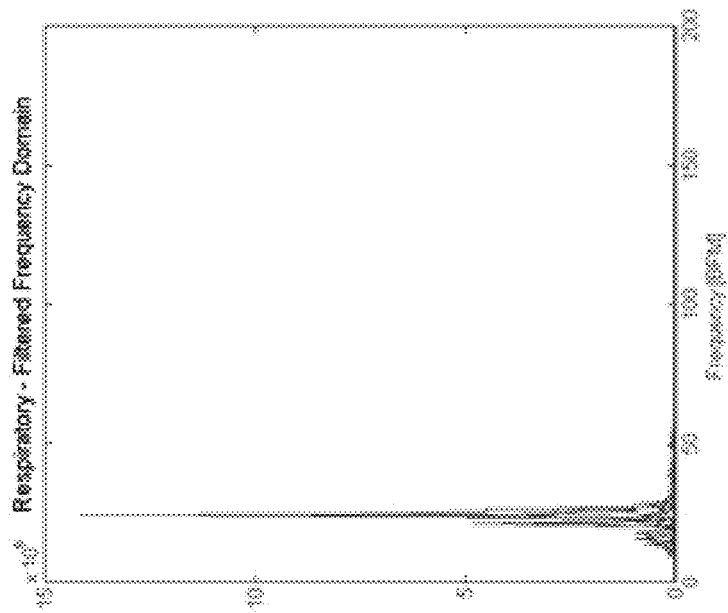
FIGS. 8A and 8B are charts showing cardiac and respiratory rates from right larynx position of the UWB sensor.
Figure 8B:
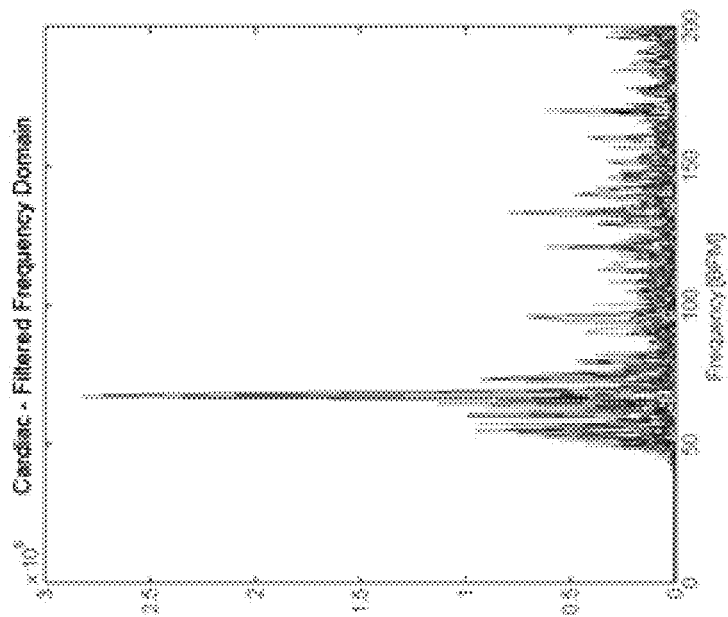

In the third test, the UWB radar sensor was placed on the right side of the animal's neck, immediately adjacent to the larynx with the axis of the sensor parallel to the longitudinal axis of the trachea. As can be seen in FIGS. 8A and 8B, the cardiac rate and pulmonary rate as calculated with an FFT were readily discernible and matched manual measurements. This position is particularly interesting because it also provides a view of the larynx, trachea, and esophagus.

Figure 9A:
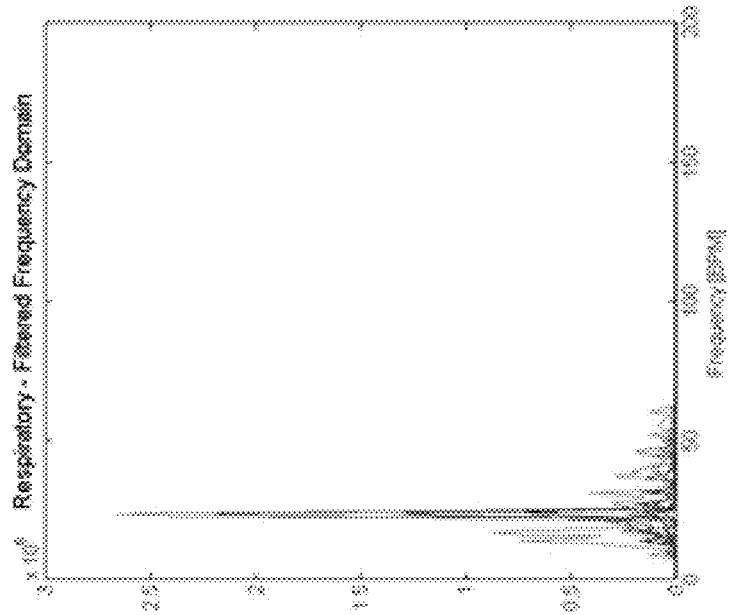
FIGS. 9A and 9B are charts showing cardiac and respiratory rates from posterior neck position of the UWB sensor.
Figure 9B:
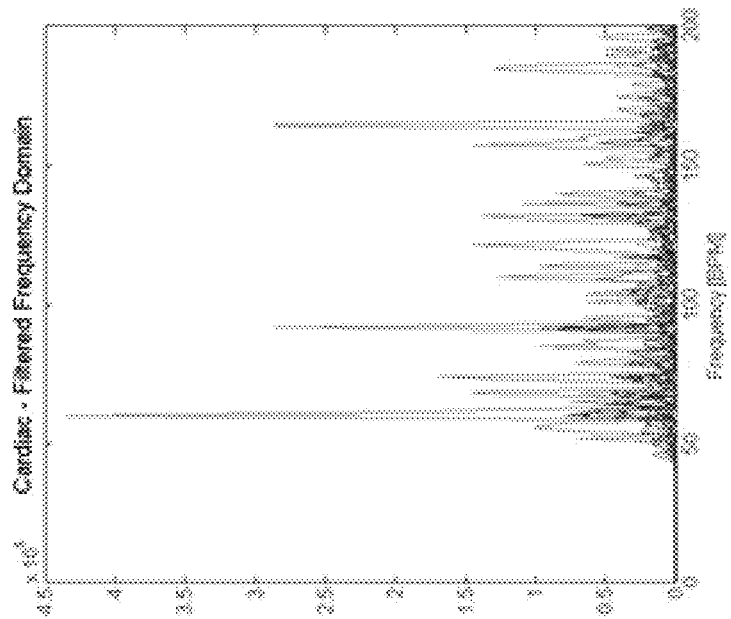

In the fourth test, the UWB radar sensor was placed on the posterior of the animal's neck, immediately over the spinous process with the axis of the sensor parallel to the longitudinal axis of the spine. As can be seen in FIGS. 9A and 9B, the cardiac rate and pulmonary rate as calculated with an FFT were readily discernible and matched manual measurements.

Figure 10A:
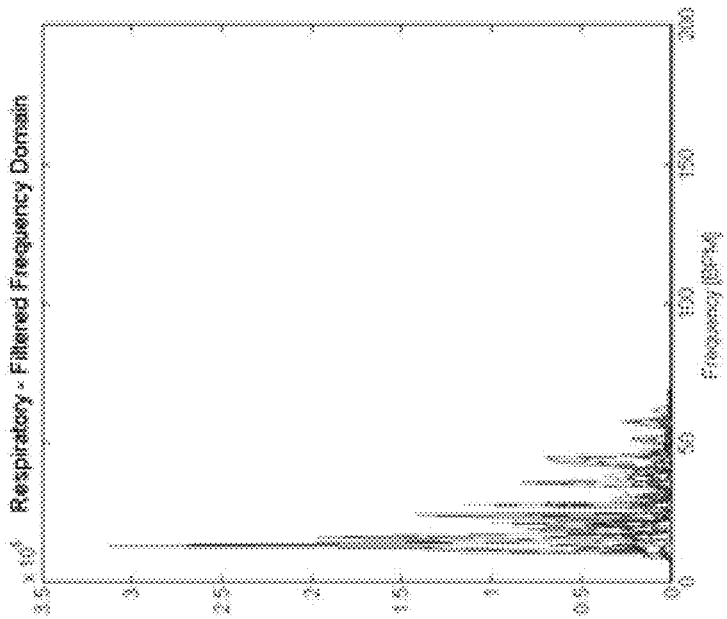
FIGS. 10A and 10B are charts showing cardiac and respiratory rates from right femoral position of the UWB sensor.
Figure 10B:
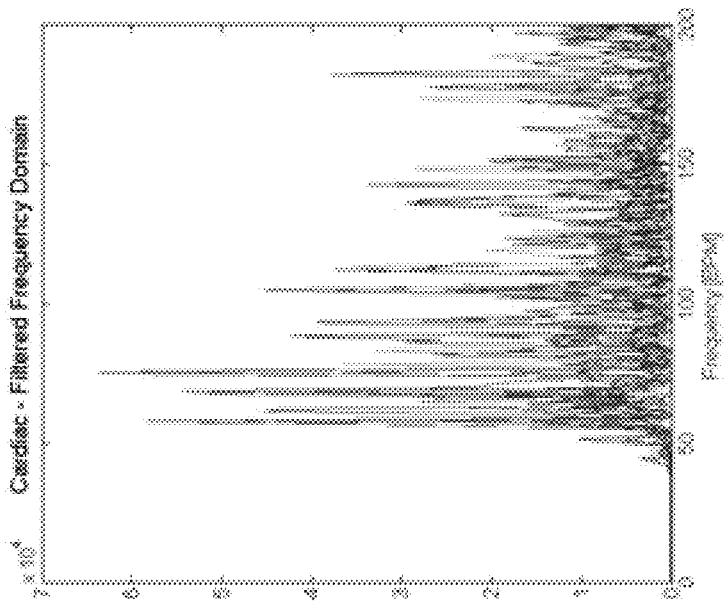

In the fifth test, the UWB radar sensor was placed on the right hind leg, immediately over the right femoral artery and below the pelvic joint, with the axis of the sensor parallel to the longitudinal axis of the artery. As can be seen in FIGS. 10A and 10B, the pulmonary rate as calculated with an FFT was readily discernible and matched manual measurements. The cardiac rate was less discernible and somewhat obscured by other noise sources.

Figure 11A:
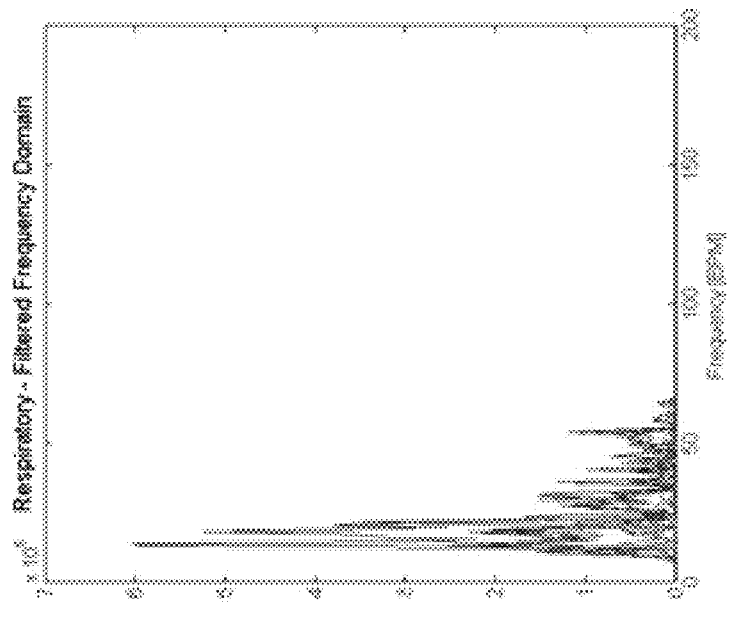
FIGS. 11A and 11B are charts showing cardiac and respiratory rates from right shoulder position of the UWB sensor.
Figure 11B:
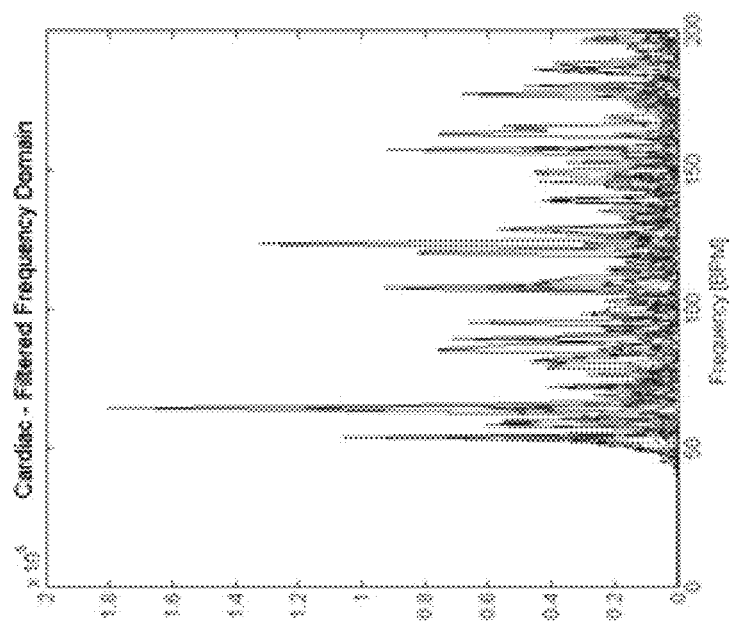

In the sixth test, the UWB radar sensor was placed on the right fore leg, immediately over the right auxiliary artery and below the shoulder joint, with the axis of the sensor parallel to the longitudinal axis of the artery. As can be seen in FIGS. 11A and 11B, the pulmonary rate as calculated with an FFT was readily discernible and matched manual measurements. The cardiac rate was less discernible and somewhat obscured by other noise sources.

To summarize these basic cardiopulmonary tests with the UWB medical radar on a canine model, the cardiac and pulmonary rates as calculated from the UWB radar data were generally discernible and matched manual measurements. In several instances, the cardiac rate was less discernible than pulmonary and somewhat obscured by other noise sources, potentially including muscle twitch from the animal and the researcher holding the sensor in position. Similarly, in several instances, the pulmonary rate varied slightly over 2-3 BPM, most likely due to the resolution of the FFT (~0.732 BPM) and the expected variability in respiration from its voluntary component (observed as minor breath-holding). It is interesting to note that the strength of the cardiac signal was typically 10-13 dB below that of the pulmonary signal while neck and torso positions produced more discernible cardiopulmonary data with minimal noise.

Figure 12:
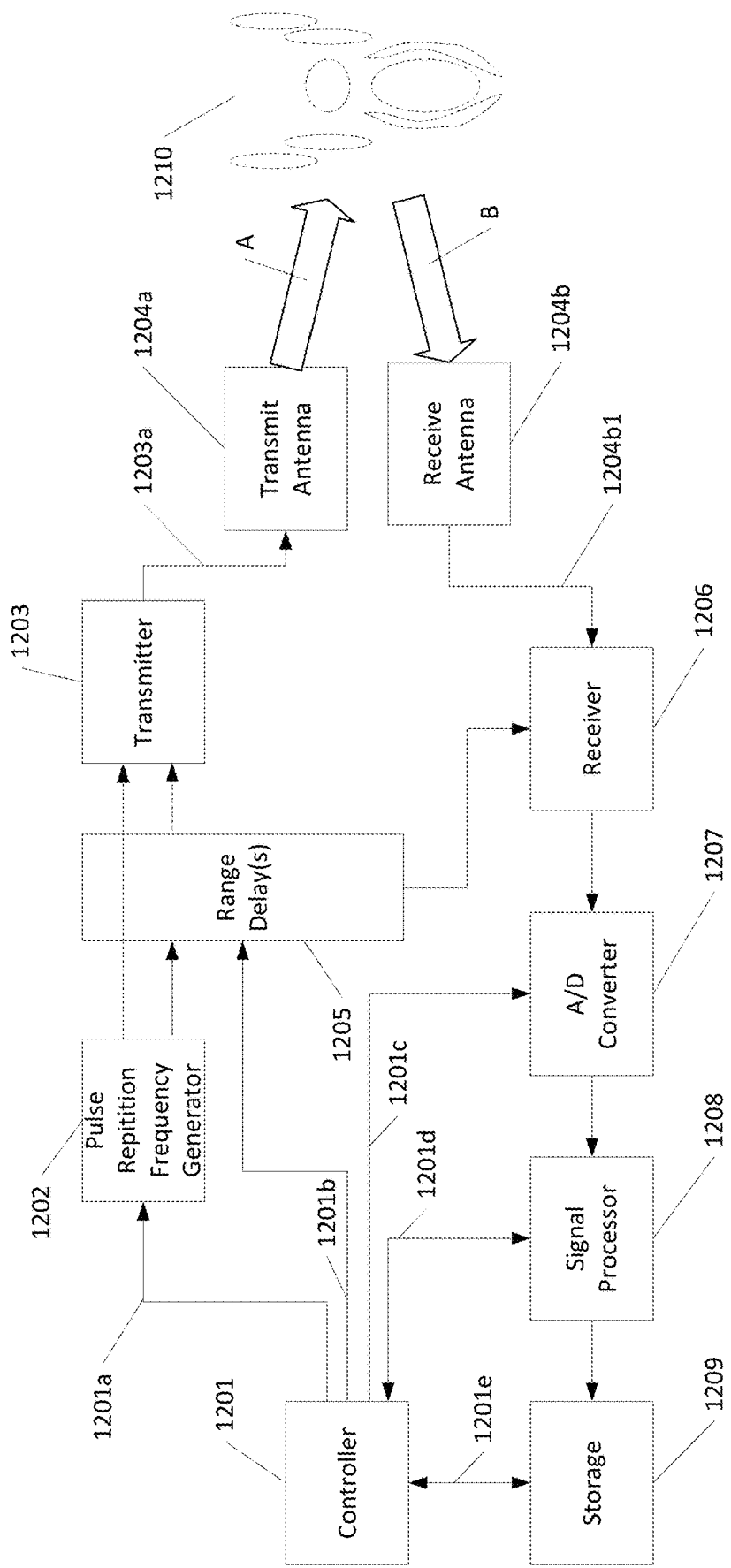
FIG. 12 shows an illustrative example of a UWB sensor.

FIG. 12 shows a conventional configuration for a UWB radar system as known in the art. The UWB radar system of U.S. Pat. No. 7,725,150 is incorporated herein by reference. The controller 1201 generates the timing and control signals 1201a, 1201b, 1201c, 1201d, and 1201e to synchronize and manage the rest of the system. It also accepts internal feedback signals from the other subsystems, accepts external control inputs from an operator, and has the capability of providing data outputs to the operator or medical record system. The controller can be realized using an integrated processor and associated circuitry.

Based on timing and control signals 1201a from the controller 1201, the pulse repetition frequency (PRF) generator 1202 creates the baseband pulse train used by the transmitter 1203 and, after range delay $\Delta t$ 1205, by the receiver 1206. Alternately, both the transmitter 1203 and the receiver 1206 may receive a delayed signal from the pulse repetition frequency generator 1202. Further, the delay applied to either or both of the transmitter 1203 and the receiver 1206 may be fixed or variable.

Since the pulse train is common to both the transmitter and receiver subsystems and allows them to operate synchronously, the system is a time-coherent radar system. In practice, a voltage-controlled oscillator (VCO) operating at a nominal but only exemplary output frequency of 2 MHz in or associated with the PRF generator supplies the pulse train. Randomized pulse-to-pulse dither can be added to the output of generator 2 by injecting a noise signal from a noise signal source (not shown) into the VCO control port. The random dither causes spectral spreading to reduce the probability of interfering with other electronic devices as well as provide a unique transmit coding pattern per unit, allowing multiple units to operate in close proximity without substantial concern for mutual interference.

Transmitter 1203 generates a series of low-voltage, short-duration pulses 1203a (in one embodiment, less than 200 ps) based on the pulse train from the PRF generator 1202. In practice, differentiating the edges of a pulse train having extremely fast rising and falling edges creates the sub-nanosecond pulses. Through the combination of the transmitter and the antenna, the short duration pulses are converted into an ultra-wide band spectrum signal centered in the RF/microwave frequency bands in accordance with FCC R&O 02-48.

In one embodiment, the transmitter 1203 and receiver 1206 share a common antenna 1204. In another embodiment, the antennas are separated into transmit antenna 1204a and receive antenna 1204b. For the transmitter, the antenna 1204a couples the short pulses from the transmitter 1203 to the environment, as illustrated at A, to a patient. Subsequently, reflections B are received from the environment and fed to the receiver 1206. Various antenna configurations may be used including: commercially available horns and flat resonators, simple magnetic dipoles, and a magnetic dipole or "loop" antenna(s) with a diameter selected to optimize the transmission and reception of UWB signals. For example, a loop antenna with a diameter of 4 cm fabricated from 24-gauge solid copper wire was used in conjunction with a UWB system operating with a 10 dB bandwidth of 1.5 Ghz to 3.4 Ghz.

Based on timing and control signals 1201b from the controller 1201 and the pulses originating from the PRF generator 1202, the range delay $\Delta t$ 1205 generates a delayed version of the PRF timing signal. The output of the range delay triggers a sample-and-hold circuit, described subsequently, in the receiver 1206 where the delay value is chosen to compensate for fixed electrical delays within the system and focus data collection to those reflections originating from a specific depth within the body. The range delay is extremely flexible and, in conjunction with the controller, can generate a large range of delay profiles to accommodate a variety of signal processing requirements.

There are two delay modes used to collect medical data-range gate mode and range finder mode. In range gate mode, the depth within the body that corresponds to the area for which physiological data is to be extracted is fixed and a large number of samples are collected at that depth over a period of multiple seconds in one example, providing information on relative changes within the body. The depth can then be changed and the process repeated. In contrast, when operating in range finder mode, the depth is swept repeatedly over a finite range of interest, with samples collected at each depth. Range gate mode provides detailed information at the depth of interest while range finder mode is used to quickly collect data over a range of depths. A range delay circuit supports both range gate and range finder modes. In practice, the range delay circuit can be realized using a 12-bit digital-to-analog converter (DAC), an operational amplifier, used to realize functions, and a one-shot multivibrator. The one-shot multivibrator (an LMC555 can be used, as one example) generates a delayed version of the transmitted pulse train in response to signals received on its two control inputs—trigger and hold-off. The pulse train from the PRF generator 1202 is the trigger signal and causes the one-shot multivibrator to initiate a single pulse cycle for each pulse in the pulse train. The hold-off voltage determines the period of the pulse. By varying the hold-off voltage, different pulse periods, and thus different delay values, can be generated. The amount of delay is set by both analog and digital controls. The analog controls set the minimum delay value and the allowable range of control while the digital controls are used to dynamically adjust the actual delay value, delay sweep rate, and resolution of delay control.

In practice, a 12-bit data value—$Data_x$, corresponding to the desired delay is sent from the controller 1201 to the DAC. The DAC produces a voltage $V_x$ where: $V_x = 4.096$ Volts$\times$($Data_x$/4096).

The DAC output voltage and a DC voltage are added together in a summing junction and the sum is amplified and fed to the hold-off control input of the one shot. The DC voltage level, in conjunction with the amplifier gain, set the minimum delay value and the allowable range of control. Both the DC voltage level and gain settings are controlled by manual adjustment of potentiometers. A delay range of 5 ns has been proven to yield good quantitative data in cardiopulmonary applications and corresponds to a depth range of approximately 12 cm into the body. Other delay range values of up to 10 ns have also shown to produce usable data sets.

The receiver 1206 processes the raw reflections received from the antennas 1204*b* over line 1204*b*1 in the analog domain to optimize the signals of interest. For cardiopulmonary data, this includes suppressing the high-strength static return signals and amplifying the motion artifacts. Receiver 1206 may be based on a dual-channel balanced receiver architecture where the transmitter pulses are capacitively coupled from the output of the transmitter 1203 into both receive channels via RF. Splitter and the antenna 1204 is connected or otherwise coupled to one channel. The balanced receiver architecture provides a high degree of common mode rejection as well as differential gain. The common mode rejection provides a significant amount of attenuation to signals common to both channels thus minimizing interference from the transmit signal with the desired receive signal. The differential gain inherent in this architecture amplifies signals unique to either channel thus the received signal, being unique to the channel, is amplified.

Both channels can use an ultra-fast sample-and-hold (S/H) circuit, each triggered by the delayed impulse train created by the pulse generator using the delayed pulse train over the line from the range delay circuit Δt 5 of FIG. 12. The active sampling window is set at approximately 320 ps in one example and can be easily modified by selectively changing the value of a single passive component. The outputs of the two S/H circuits are integrated over multiple samples in integrator elements to improve the signal-to-noise ratio. The integrated samples feed the inverting and non-inverting inputs of an instrumentation amplifier, attenuating the transmitted signal and amplifying the received signal.

As illustrated in FIG. 12, A/D converter 1207 (ADC) is controlled by controller 1201 through control lines 1201*c*. The controller sets the sample rate, sample resolution, and start/stop timing for the sampling process based on the mode of operation. The ADC digitizes the enhanced analog motion reflections from the receiver 1206, translating the enhanced reflected energy into a series of discrete digital values. As one example in range gate mode, 16,000 samples per second at 16-bits per sample may be used.

The digitized signal from the A/D converter 1207 is then processed to extract pertinent physiological information in signal processor 1208 per FIG. 12. The signal processing block is extremely flexible and, as mentioned previously, can accommodate a wide variety of algorithms in support of different medical applications. In addition the algorithm can be implemented using parallel, serial, or hybrid parallel/serial architecture. The choice of a specific architecture is left to those skilled in the art and will depend on the application and other system constraints. The controller manages the signal processing operations through control path 1201*d*.

The resultant physiological data is displayed on a user interface (not shown). This can include tracings of amplitude versus time for one or more depths of interest, power spectral density for one or more depths of interest, time domain and frequency domain histograms for a range of depths, numerical values for heart and/or lung rates, as well as the associated confidence factors for the displayed data, as described subsequently. The controller 1201 of FIG. 12 converts the data from the signal processor to an operator-friendly format through control path 1201*e* for display on the user interface.

What is claimed is:

1. A wearable device comprising:
   a processor configured to control generation of an ultra-wideband radar signal and reception of one or more resultant signals;
   a transmit antenna configured to output the ultra-wideband radar signal directed at biological tissue; and
   a receive antenna configured to receive the one or more resultant signals based on a reflection of the ultra-wideband radar signal from the biological tissue,
   wherein the transmit antenna is angled relative to the receive antenna.

2. The wearable device of claim 1, wherein the processor is configured to determine a heart rate based on determining, using the one or more resultant signals, expansion and contraction of arteries.

3. The wearable device of claim 1, wherein the processor is configured to determine a respiration rate.

4. The wearable device of claim 1, wherein the processor is configured to apply beam-steering or beam-forming to the generation of the ultra-wideband radar signal.

5. The wearable device of claim 1, comprising:
a housing, wherein the housing contains the processor.

6. The wearable device of claim 5, wherein the housing contains the transmit antenna and the receive antenna.

7. The wearable device of claim 5, wherein the housing is a moisture-resistant housing.

8. An apparatus comprising:
a processor configured to control generation of an ultra-wideband radar signal and reception of one or more resultant signals;
a transmit antenna configured to output the ultra-wideband radar signal directed at biological tissue; and
a receive antenna configured to receive the one or more resultant signals based on a reflection of the ultra-wideband radar signal from the biological tissue, wherein the transmit antenna is angled relative to the receive antenna.

9. The apparatus of claim 8, wherein the processor is configured to determine a heart rate based on determining, using the one or more resultant signals, expansion and contraction of arteries.

10. The apparatus of claim 8, wherein the processor is configured to determine a respiration rate.

11. The apparatus of claim 8 wherein the processor is configured to apply beam-steering or beam-forming to the generation of the ultra-wideband radar signal.

12. The apparatus of claim 8, comprising:
a housing, wherein the housing contains the processor.

13. The apparatus of claim 12, wherein the housing contains the transmit antenna and the receive antenna.

14. The apparatus of claim 12, wherein the housing is a moisture-resistant housing.

* * * * *